US007906319B2

(12) United States Patent  (10) Patent No.: US 7,906,319 B2
Hasson et al.  (45) Date of Patent: Mar. 15, 2011

(54) SYSTEMS AND METHODS FOR MONITORING THE AMPLIFICATION AND DISSOCIATION BEHAVIOR OF DNA MOLECULES

(75) Inventors: Kenton C. Hasson, Gaithersburg, MD (US); Gregory A. Dale, Gaithersburg, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 1138 days.

(21) Appl. No.: 11/606,204

(22) Filed: Nov. 30, 2006

(65) Prior Publication Data

US 2008/0003594 A1   Jan. 3, 2008

Related U.S. Application Data

(60) Provisional application No. 60/806,440, filed on Jun. 30, 2006.

(51) Int. Cl.
  *C12M 1/34* (2006.01)
  *C12M 3/00* (2006.01)
(52) U.S. Cl. .............. 435/287.2; 435/5; 435/6; 435/7.1
(58) Field of Classification Search ............. 435/5–7.1, 435/287.2–288.7
See application file for complete search history.

(56) References Cited

U.S. PATENT DOCUMENTS

| | | | |
|---|---|---|---|
| 6,174,670 B1 * | 1/2001 | Wittwer et al. ................. 435/6 |
| 6,271,022 B1 | 8/2001 | Bochner | |
| 6,689,565 B2 | 2/2004 | Nikiforov | |
| 6,713,264 B2 | 3/2004 | Luttermann et al. | |
| 6,979,567 B2 | 12/2005 | Herron et al. | |
| 7,081,954 B2 | 7/2006 | Sandstrom | |
| 7,090,133 B2 | 8/2006 | Zhu | |
| 7,160,998 B2 * | 1/2007 | Wittwer et al. ............ 536/24.3 |
| 2001/0036231 A1 | 11/2001 | Easwar et al. | |
| 2003/0104466 A1 * | 6/2003 | Knapp et al. .................. 435/6 |
| 2003/0199081 A1 * | 10/2003 | Wilding et al. ............ 435/287.2 |
| 2004/0096854 A1 * | 5/2004 | Choong et al. ................ 435/6 |
| 2005/0009101 A1 * | 1/2005 | Blackburn .................. 435/7.1 |
| 2005/0042639 A1 * | 2/2005 | Knapp et al. .................. 435/6 |
| 2005/0117049 A1 | 6/2005 | Suzuki | |
| 2005/0135655 A1 | 6/2005 | Kopf-Sill et al. | |
| 2005/0164281 A1 * | 7/2005 | Oh et al. .................... 435/6 |
| 2005/0189224 A1 | 9/2005 | Parce | |
| 2005/0221373 A1 | 10/2005 | Enzelberger et al. | |
| 2005/0231723 A1 | 10/2005 | Blasenheim et al. | |
| 2005/0233335 A1 * | 10/2005 | Wittwer et al. ................ 435/6 |
| 2006/0000722 A1 | 1/2006 | Parce et al. | |
| 2006/0006067 A1 | 1/2006 | Unger | |
| 2006/0223166 A1 * | 10/2006 | Wilding et al. ............ 435/287.1 |
| 2006/0257893 A1 * | 11/2006 | Takahashi et al. ............ 435/6 |
| 2007/0026421 A1 * | 2/2007 | Sundberg et al. ............ 435/6 |

* cited by examiner

*Primary Examiner* — Walter D Griffin
*Assistant Examiner* — Shanta G Doe
(74) *Attorney, Agent, or Firm* — Rothwell, Figg, Ernst & Manbeck, pc

(57) ABSTRACT

The present invention relates to systems and methods for monitoring the amplification of DNA molecules and the dissociation behavior of the DNA molecules. The present invention in one embodiment provides a system that includes a microfluidic channel comprising a PCR processing zone and an HRTm analysis zone; and an image sensor having a first image sensor region having a first field of view and a second image sensor region having a second field of view, wherein the second field of view is different than the first field of view, wherein at least a portion of the PCR processing zone is within the first field of view; and at least a portion of the HRTm analysis zone is within the second field of view.

21 Claims, 8 Drawing Sheets

SYSTEMS AND METHODS FOR MONITORING THE AMPLIFICATION AND DISSOCIATION BEHAVIOR OF DNA MOLECULES

CROSS REFERENCE TO RELATED APPLICATION(S)

The present application claims the benefit to U.S. Provisional Patent Application Ser. No. 60/806,440, filed on Jun. 30, 2006, which is incorporated herein by this reference.

BACKGROUND

1. Field of the Invention

The present invention relates to systems and methods for monitoring the amplification of DNA molecules and the dissociation behavior of the DNA molecules.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA.

With PCR, one can quickly produce millions of copies of DNA starting from a single template DNA molecule. PCR includes a three phase temperature cycle of denaturation of the DNA into single strands, annealing of primers to the denatured strands, and extension of the primers by a thermostable DNA polymerase enzyme. This cycle is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

In some applications, it is important to monitor the accumulation of DNA products as the amplification process progresses. Real-time PCR refers to a growing set of techniques in which one measures the buildup of amplified DNA products as the reaction progresses, typically once per PCR cycle. Monitoring the amplification process over time allows one to determine the efficiency of the process, as well as estimate the initial concentration of DNA template molecules. For general details concerning real-time PCR see *Real-Time PCR: An Essential Guide*, K. Edwards et al., eds., Horizon Bioscience, Norwich, U.K. (2004).

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Anal Chem* 73:565-570 (2001)), Kopp et al. (*Science* 280:1046-1048 (1998)), Park et al. (*Anal Chem* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Once there are a sufficient number of copies of the original DNA molecule, the DNA can be characterized. One method of characterizing the DNA is to examine the DNA's dissociation behavior as the DNA transitions from double stranded DNA (dsDNA) to single stranded DNA (ssDNA) with increasing temperature. The process of causing DNA to transition from dsDNA to ssDNA is sometimes referred to as a "high-resolution temperature (thermal) melt (HRTm)" process, or simply a "high-resolution melt" process.

Accordingly, what is desired is a system for monitoring the DNA amplification process and for determining the DNA's dissociation behavior.

SUMMARY OF THE INVENTION

The present invention relates to systems and methods for performing and monitoring real-time PCR and HRTm analysis.

In one aspect, the present invention provides a system that includes the following elements: a microfluidic channel comprising a PCR processing zone and an HRTm analysis zone; and an image sensor having a first image sensor region having a first field of view and a second image sensor region having a second field of view, wherein the second field of view is different than the first field of view, wherein at least a portion of the PCR processing zone is within the first field of view; and at least a portion of the HRTm analysis zone is within the second field of view. In one embodiment, the system may further include: a first thermal generating apparatus configured to provide heat to and/or absorb heat from the PCR processing zone; and a second thermal generating apparatus configured to provide heat to and/or absorb heat from the HRTm analysis zone. The two temperature generating apparatuses may be operated independently so that HRTm analysis can occur in the HRTm analysis zone while at the same time PCR is occurring in the PCR processing zone. The system may also include an image sensor controller configured such that, for each bolus that undergoes HTRm analysis in the HRTm analysis zone, the image sensor controller preferably captures at least about 10 images per second from the second image sensor region for at least about 1 minute while the bolus undergoes the HRTm analysis. In some embodiments, to achieve the 10 images/second capture rate, the controller may window the image sensor. In some embodiments, the system may further include a lens that is disposed between the channel and the image sensor. In such embodiments, the lens may be configured to focus onto the first image sensor region only the light coming from the PCR processing zone and to focus onto the second image sensor region only the light coming from the HRTm analysis zone.

In another aspect, the present invention provides a system that includes (i) a channel for receiving a bolus of solution containing real-time PCR reagents, which channel includes a DNA amplification zone and a DNA melting zone adjacent to the DNA amplification zone, and (ii) an image sensor disposed in relation to the channel such that both the DNA melting zone and the DNA amplification zone are within the field of view of the sensor at the same time. In some embodiments, the system may further include: a first thermal generating apparatus configured to provide heat to and/or absorb heat from the DNA amplification zone; and a second thermal generating apparatus configured to provide heat to and/or absorb heat from the DNA melting zone. The two temperature generating apparatuses may be operated independently so that DNA melting can occur in the DNA melting zone while at the same time DNA amplification is occurring in the DNA amplification zone. In some embodiments, the first thermal generating apparatus is configured such that while a bolus is within the DNA amplification zone, the first thermal generating apparatus cycles the temperature in the DNA amplification zone in order to achieve PCR, and the second thermal generating apparatus is configured such that, when a bolus enters the DNA melting zone, the second thermal generating apparatus provides a substantially steadily increasing amount of heat to the DNA melting zone at a thermal ramp rate of typically 0.1 to 1 degree Celsius (C.) per second. In some embodiments, the length of the DNA melting zone is significantly smaller than the length of the DNA amplification zone (e.g., the length of the DNA melting zone may be ⅕ the length of the DNA amplification zone. In some embodiments, the system includes an image controller. The image controller may be configured such that, for each bolus that enters the melting zone, the controller preferably captures at least about 10 images per second from the second image sensor region for at least about 1 minute. In some embodiments, to achieve the 10 images/second capture rate, the controller may window the image sensor.

In another aspect, the present invention provides a method that includes the steps of: (a) using a PCR processing zone of a channel to perform a PCR process; (b) using an HRTm analysis zone of the channel to perform an HRTm process; (c) while performing step (b) using an image sensor to obtain images of the HRTm analysis zone; and (d) after performing step (c) and without moving the image sensor from the position it was in relative to the channel when step (c) was performed, using the image sensor to obtain images of and the PCR processing zone while performing step (a). In some embodiments, the step of using the PCR processing zone to achieve PCR includes the steps of: moving a bolus of test solution containing real-time PCR reagents through the PCR processing zone; and cycling the temperature of the bolus while the bolus is in the PCR processing zone, and the step of using the HRTm analysis zone to perform an HRTm process includes the steps of: moving a bolus of test solution containing real-time PCR reagents through the HRTm analysis zone; and steadily increasing the temperature of the bolus while the bolus is in the HRTm analysis zone. In some embodiments, the step of cycling the temperature of the bolus in order to achieve PCR comprises using a first thermal generating apparatus to cycle the temperature, and the step of steadily increasing the temperature of the bolus comprises using a second thermal generating apparatus to steadily increase the temperature. In some embodiments, the method may further include the steps of causing a bolus of solution containing real-time PCR reagents to move through the PCR processing zone and then through the HRTm analysis zone, and using the image sensor to capture at least about 10 images of the bolus per second for at least about 1 minute while the bolus is in the HRTm analysis zone.

In another aspect, the present invention provides a method that includes the steps of: (a) performing a PCR process in a first zone of a microfluidic channel; (b) performing an HRTm process in a second zone of the microfluidic channel; (c) while performing step (a), focusing radiation from the first zone onto a first region of an image sensor, but not onto a second region of the image sensor; and (d) while performing step (c), focusing radiation from the second zone onto the second region of the image sensor, but not onto the first region of the image sensor.

In some embodiments, the step of performing the PCR process in the first zone comprises: moving a bolus of test solution containing real-time PCR reagents through the first zone; and, while the bolus is in the first zone, cycling the temperature of the bolus in order to achieve PCR; and the step of performing an HRTm process in the second zone comprises: moving a bolus of test solution containing real-time PCR reagents through the second zone after moving the bolus through the first zone; and while the bolus is in the second zone, steadily increasing the temperature of the bolus. In some embodiments, the step of cycling the temperature of the bolus in order to achieve PCR comprises using a first thermal generating apparatus to cycle the temperature, and the step of steadily increasing the temperature of the bolus comprises using a second thermal generating apparatus to steadily increase the temperature. In some embodiments, the method further includes: causing a bolus of solution containing real-time PCR reagents to move through the first zone and then through the second zone, and using the image sensor to capture preferably at least about 10 images of the bolus per second for at least about 1 minute while the bolus is in the second zone.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of a reference number identifies the drawing in which the reference number first appears.

DETAILED DESCRIPTION OF PREFERRED EMBODIMENTS

Figure 1:
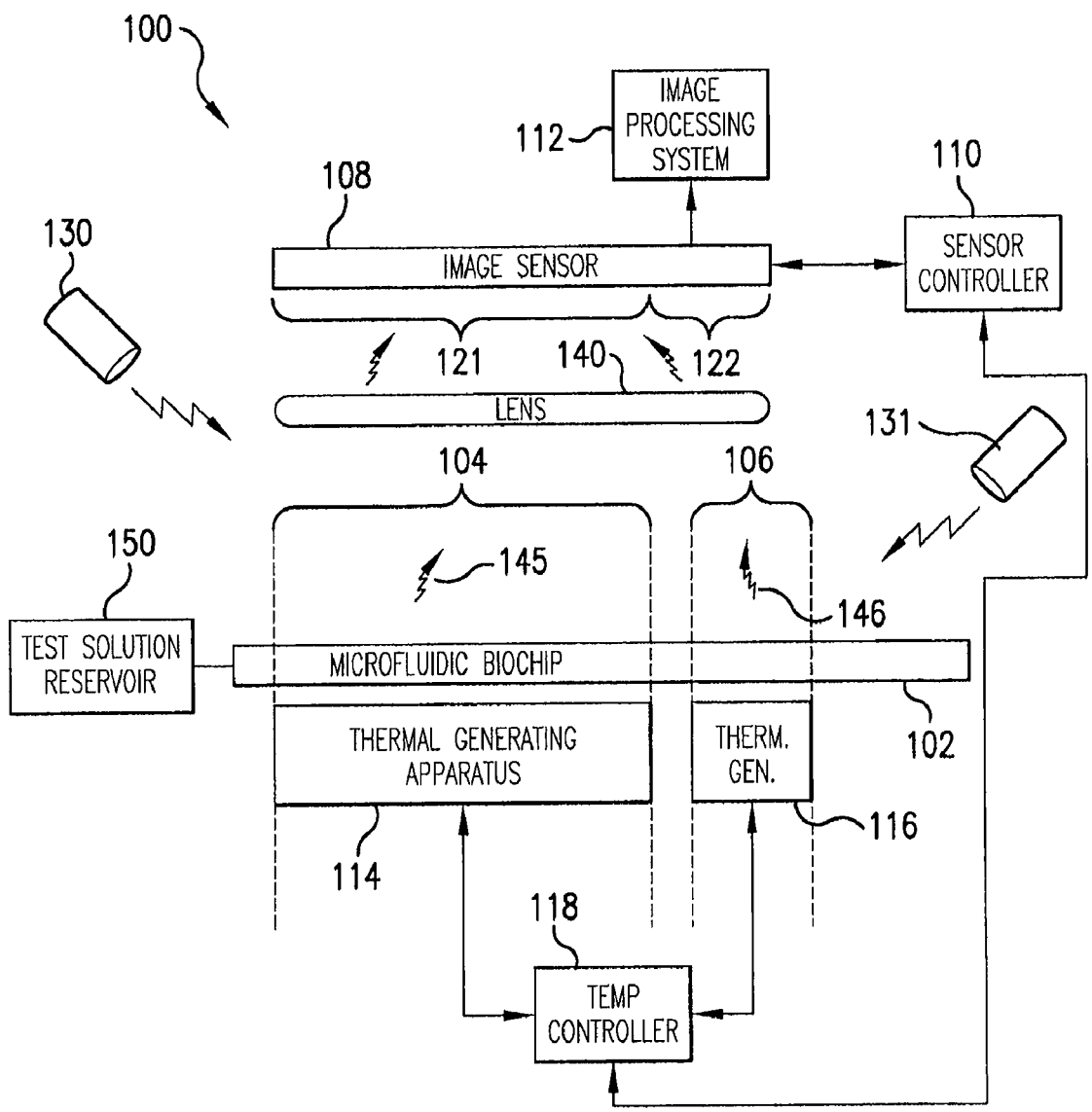
FIG. 1 is a functional block diagram of a genomic analysis system according to one embodiment.

Referring to the drawings, FIG. 1 illustrates a nucleic acid analysis system 100 according to an embodiment. As shown in FIG. 1, system 100 includes a microfluidic biochip 102 having a PCR processing zone 104 (i.e., a zone in which DNA is amplified) and a HRTm analysis zone 106 (i.e., a zone in which the dissociation behavior of the amplified DNA is examined).

Figure 2:
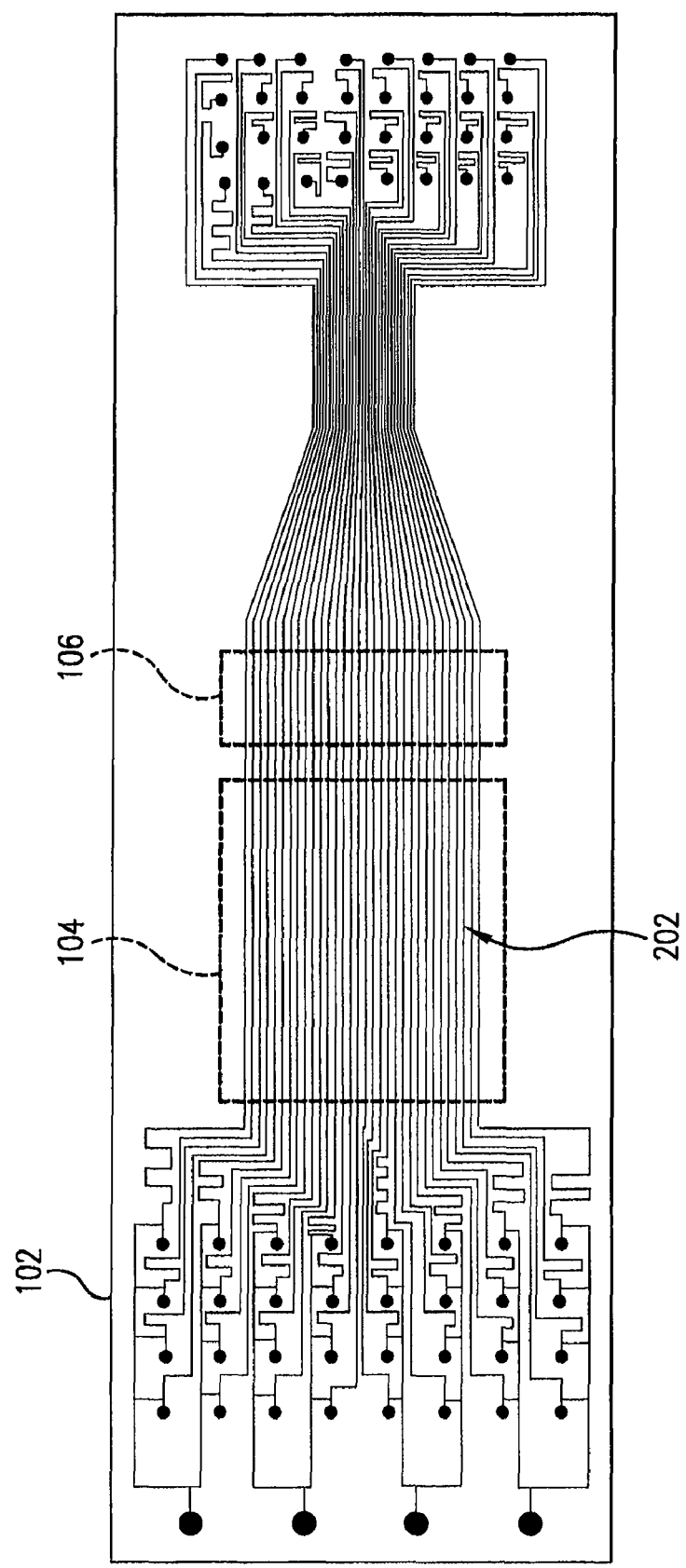
FIG. 2 is a top view of a biochip according to one embodiment.

FIG. 2 is a top view of biochip 102 according to some embodiments. As shown in FIG. 2, biochip 102 includes a number of microfluidic channels 202. In the example shown, there are 8 microfluidic channels, but it is contemplated that chip 102 may have more or less than 8 channels. As shown, a first portion of each microfluidic channel may be within the PCR processing zone 104 and a second portion of each microfluidic channel may be within the HRTm analysis zone 106. As further shown in FIG. 1, zone 106 may immediately follow zone 104 and the length of zone 104 may be significantly greater than the length of zone 106 (e.g., the length of zone 104 may be 5 times the length of zone 106).

Although FIG. 1 shows that there is a small gap between zones 104 and 106, it is contemplated that there no gap exists between the zones (i.e., it is contemplated that zone 106 not only immediately follows zone 104, but also shares a common boundary with zone 104).

In some embodiments, when system 100 is in use, at least one channel 202 receives a sample (or "bolus") of a solution containing real-time PCR reagents. A force may be used to cause the bolus to travel through the channel such that the bolus traverses PCR zone 104 prior to entering HRTm zone 106. One system and method for performing PCR in a microfluidic device is disclosed in U.S. patent application Ser. No. 11/505,358, filed on Aug. 17, 2006, incorporated herein by reference.

Referring back to FIG. 1, genomic analysis system 100 further includes an image sensor 108, a controller 110 for controlling image sensor 108, and an image processing system 112 for processing the image data produced by image sensor 108. Image sensor 108 may be implemented using a CMOS image sensor, a CCD image sensor, or other image sensor. For example, in one embodiment, sensor 108 is a CMOS sensor with an effective 12.7 mega pixel resolution and having a size of 36×24 mm, which is available from Canon Inc.

Image sensor 108 has a first image sensor region 121 and a second image sensor region 122. Image sensor region 121 has a different field of view than image sensor region 122. In preferred embodiments, image sensor 108 is positioned with respect to chip 102 such that at least a portion of PCR processing zone 104 is within the field of view of sensor region 121 and at least a portion of HRTm zone 106 is within the field of view of sensor region 122.

Figure 3:
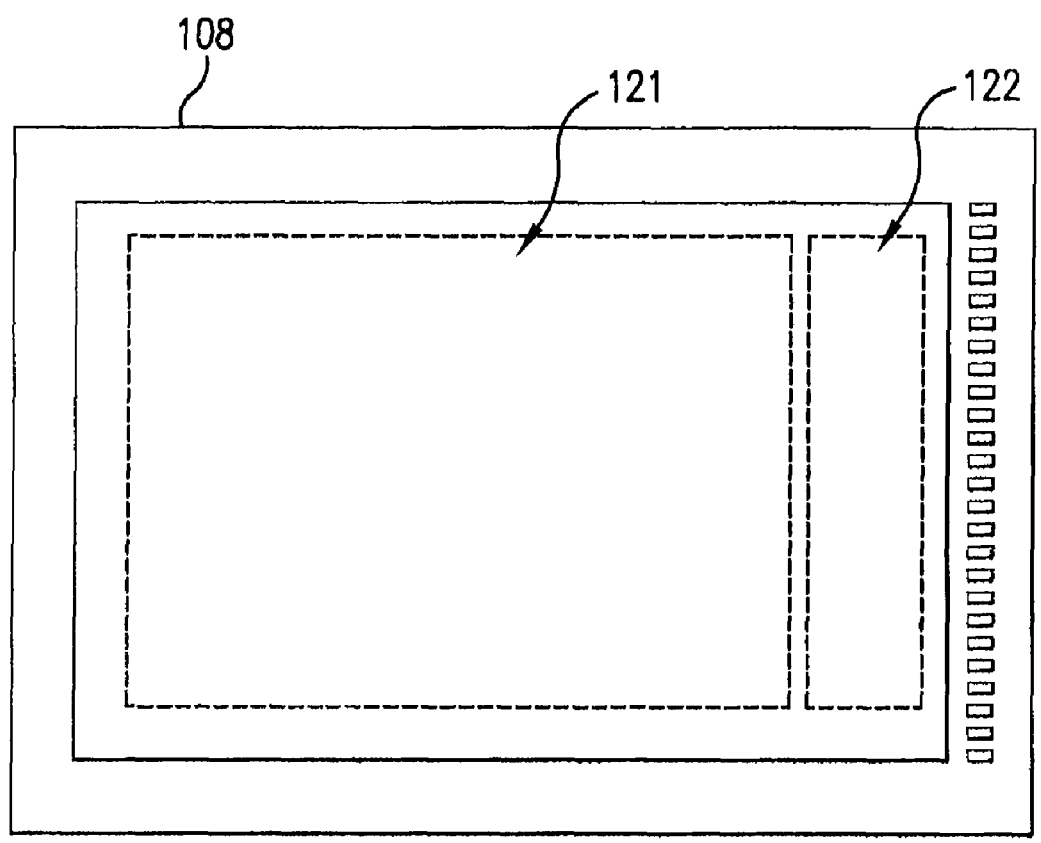
FIG. 3 is a view of an image sensor according to one embodiment.

Referring now to FIG. 3, FIG. 3 is a view of the light sensitive surface of image sensor 108. This view better illustrates the two image sensor regions 121, 122. As shown, the area of image sensor region 122 may be significantly smaller than the area of image sensor region 121 (e.g., ⅕ the area or less). In some embodiments the widths of the two regions 121, 122 are the same, but the lengths are different.

Figure 8:
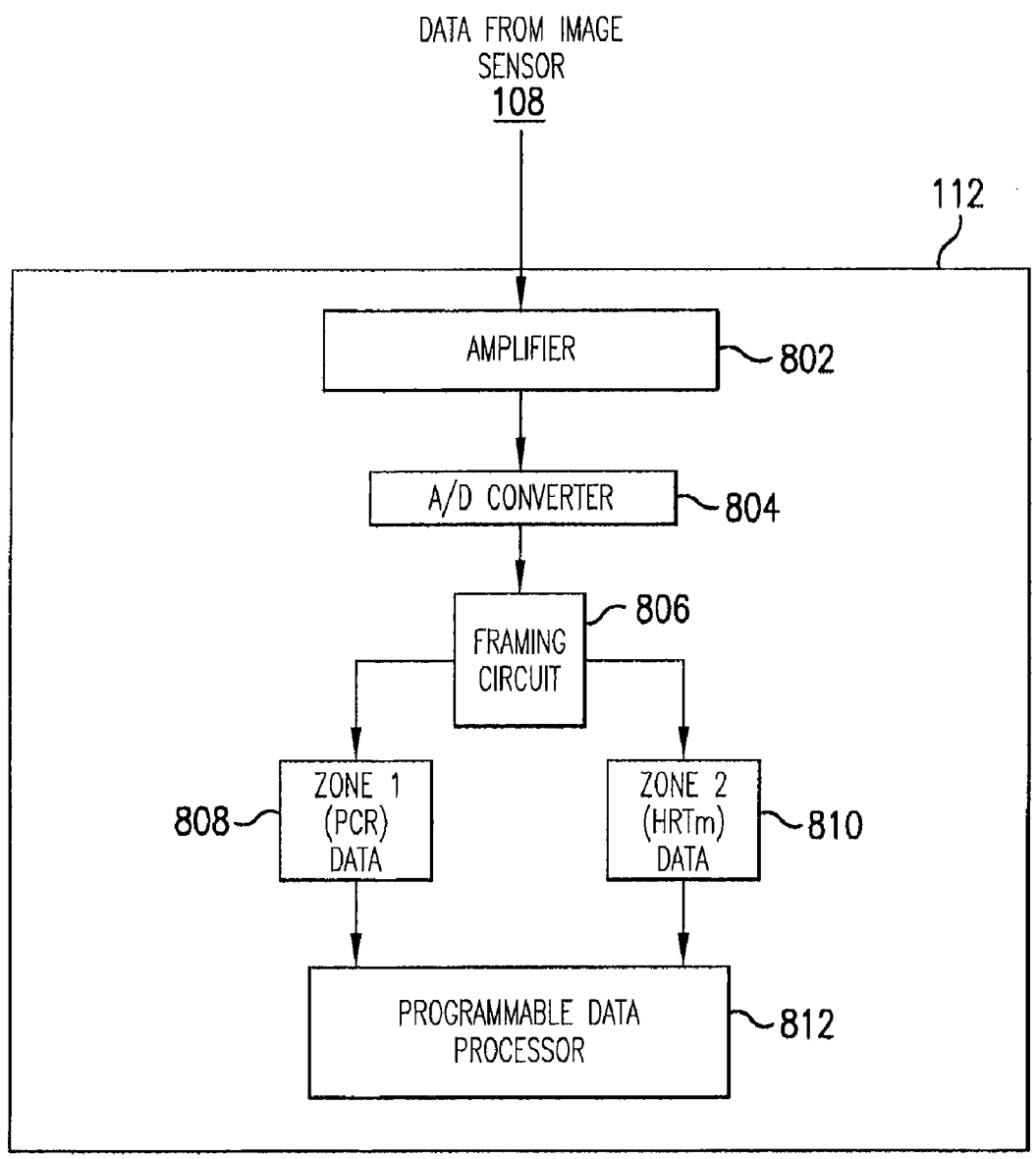
FIG. 8 is a functional block diagram illustrating an embodiment of image processing system.

Referring now to FIG. 8, FIG. 8 is a functional block diagram illustrating an embodiment of image processing system 112. As shown in FIG. 8, system 112 receives data output from image sensor 108. System 112 may include an amplifier 802 to amplify the data from image sensor 108. In one non-limiting embodiment, amplifier 802 may amplify the data for greater than 3200 ISO sensitivity. The amplified data may be converted to a digital signal by, for example, a 16 bit analog-to-digital (A/D) converter 804. In one embodiment, utilization of a 16 bit A/D converter provides a high level of dynamic range and low end bit resolution. The digital signal output from A/D converter 804 may be processed by a framing circuit 806, which may be configured to store data produced from image sensor region 121 in a zone 1 data buffer 808 and store data produced from image sensor region 122 in a zone 2 data buffer 810. A programmable data processor 812 may be programmed to process data in buffers 810 and 812 to, among other things, determine and record the intensity of the fluorescence from zones 104 and 106.

By configuring image sensor 108 and chip 102 as described above, a single image sensor is able to (i) produce data corresponding to the intensity of emissions from PCR zone 104 and (ii) produce data corresponding to the intensity of emissions from HRTm zone 106. Thus, while utilizing only a single image sensor, system 100 can simultaneously monitor (1) the amplification of a sample of DNA and (2) the dissociation behavior of a different DNA sample.

As further illustrated in FIG. 1, system 100 may include one or more thermal generating apparatuses. In the embodiment shown, system 100 includes a first thermal generating apparatus 114 and a second thermal generating apparatus 116 and a controller 118 for controlling apparatuses 114, 116. In one embodiment, first thermal generating apparatus creates a first thermal zone in PCR processing zone 104 and second thermal generating apparatus creates a second thermal zone in the HRTm analysis zone 106.

Each thermal generating apparatus 114, 116 is configured to provide heat to and/or absorb heat from chip 102, and, thus, may include one or more heat sources and/or heat sinks (e.g., each thermal generating apparatus 114, 116 may include a peltier device or other heat source or sink). More specifically, in the embodiment shown, thermal apparatus 114 is configured to provide heat to and/or absorb heat from PCR zone 104, and thermal apparatus 116 is configured to provide heat to and/or absorb heat from HRTm zone 106.

While only one temperature controller is shown, it is contemplated that each thermal generating apparatus may have its own controller. Additionally, although system 100 may have a single temperature controller, the thermal generating apparatuses may be operated independently so apparatus 116 can be used to perform HRTm analysis in zone 106 while at the same time apparatus 114 is used to cause PCR to occur in zone 104.

That is, in some embodiments, the first thermal generating apparatus 114 is configured such that while a bolus is within zone 104, thermal generating apparatus 114 cycles the temperature in zone 104 to achieve PCR, and thermal generating apparatus 116 is configured such that, when a bolus enters zone 106, thermal generating apparatus 116 provides a substantially steadily increasing amount of heat to zone 106 to cause the bolus to undergo HRTm analysis (i.e., to cause the dsDNA in the bolus to transition to ssDNA). In one example, thermal generating apparatus 116 may provide a thermal ramp rate of typically 0.1 to 2 degree Celsius (C.) per second, with the preferred ramp rate being between 0.5 and 1 degree Celsius (C.) per second.

Referring now to sensor controller 110, sensor controller 110 may be configured so that, for each bolus that undergoes HTRm analysis in the HRTm analysis zone, image sensor controller 110 causes sensor 108 to capture preferably at least about 10 images per second from image sensor region 122 for at least about 1 minute while the bolus undergoes the HRTm analysis (typically it captures the images for an uninterrupted duration of about 5 minutes). In embodiments where the ramp rate is faster, the image sensor controller 110 may cause sensor 108 to capture the images at a rate of about 20 images per second. In many embodiments, the goal is to achieve a temperature resolution of 0.1 degree Celsius or better.

In some embodiments, to achieve the high 10 images/second frame rate, the sensor may be implemented using a CMOS sensor and the controller may be configured to window the CMOS sensor to read out only the pixels of interest (e.g., some or all of the pixels within image sensor region 122).

In some embodiments, system 100 may further include an excitation source 130 (e.g., a laser or other excitation source) for illuminating zones 104 and/or 106. Additional excitation sources (e.g., source 131) may also be employed. System 100 may further include a lens 140 that is disposed between chip 102 and image sensor 108. In such embodiments, lens 140 may be configured to focus onto the first image sensor region 121 light 145 coming from the PCR processing zone 104 and to focus onto the second image sensor region 122 light 146 coming from the HRTm analysis zone 106.

Figure 4:
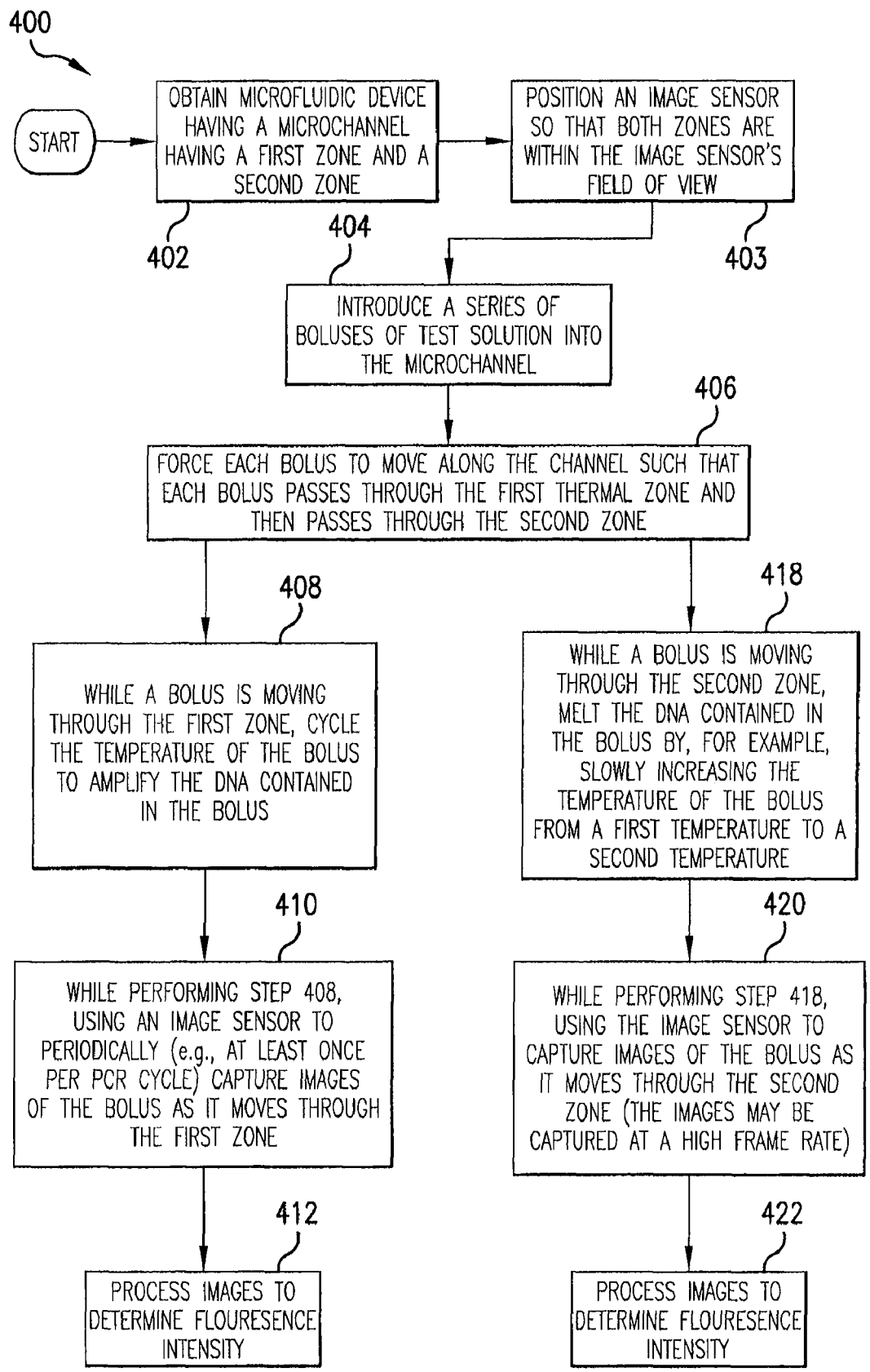
FIG. 4 is a flow chart illustrating a process according to one embodiment.
Figure 5:
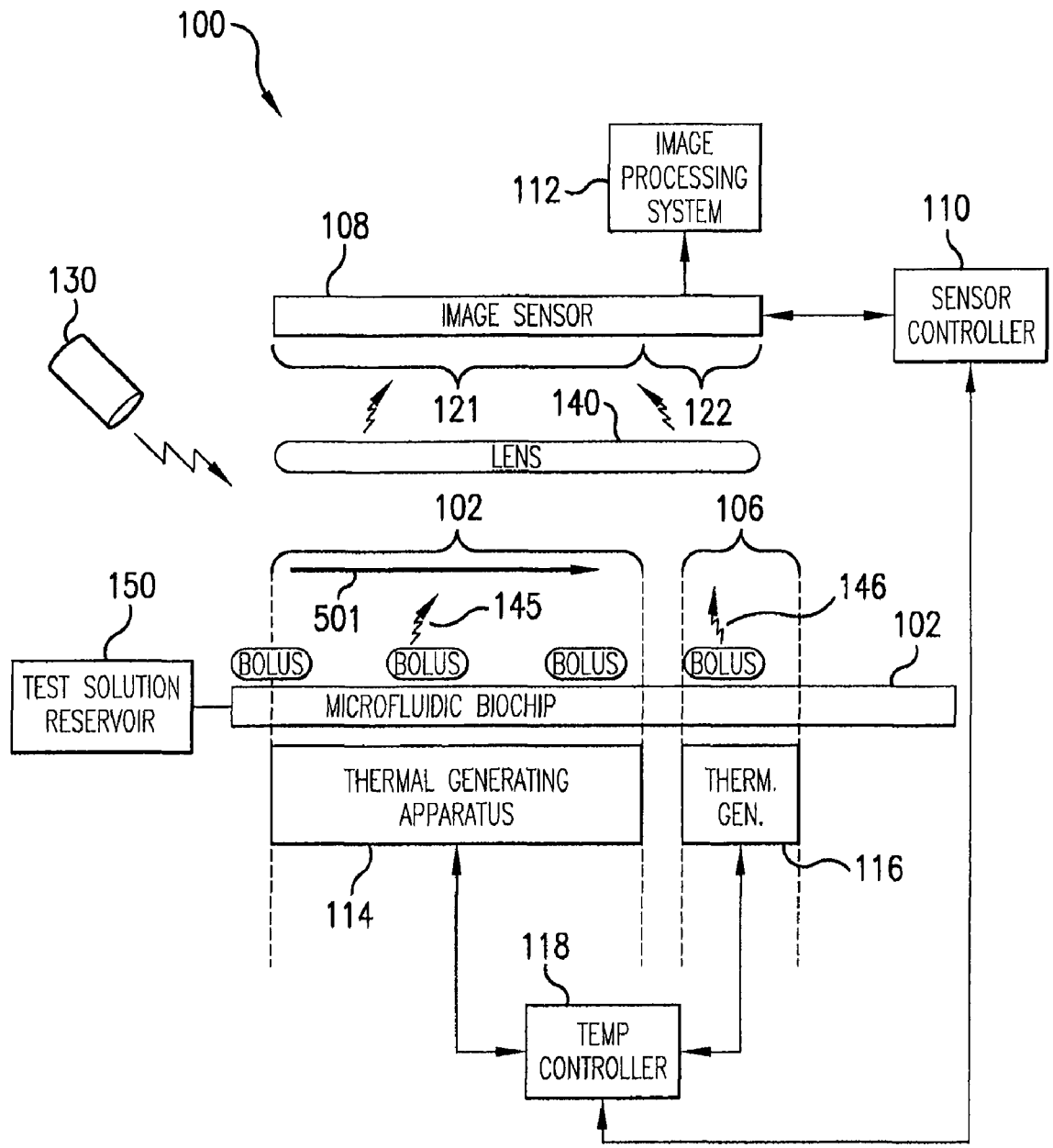
FIG. 5 is functional block diagram of a genomic analysis system according to one embodiment.

Referring now to FIG. 4, FIG. 4 is a flow chart illustrating a process 400 according to an embodiment. Process 400 may begin in step 402, where a microfluidic device 102 having a microchannel having a PCR processing zone 104 (the first thermal zone) and a HRTm analysis zone 106 (the second thermal zone) is obtained (see FIG. 5). In step 403, an image sensor (e.g., image sensor 108) is obtained and positioned such that both the first and second thermal zones are simultaneously within the image sensor's field of view.

In step 404, a series of boluses of a test solution are introduced into the microchannel (the test solution may be stored in a test solution reservoir 150 (see FIG. 1)). In step 406, each bolus is forced to move along the channel such that each bolus passes through the PCR processing zone and then enter and moves through the HRTm analysis zone. This step is pictorially illustrated in FIG. 5. Arrow 501 shows the direction in which the series of boluses move. In some embodiments, the boluses continuously move at a constant speed.

Figure 6:
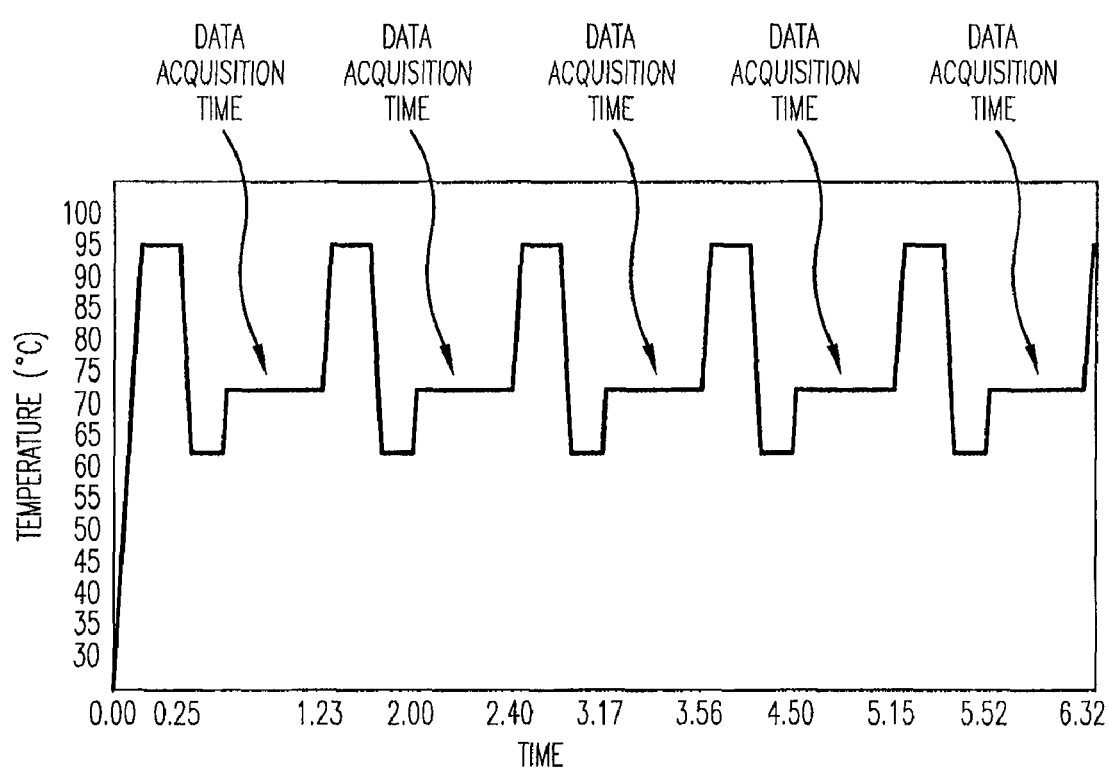
FIG. 6 illustrates a first temperature profile according to one embodiment.

In step 408, while one or more boluses are moving through the PCR processing zone, the temperature of the PCR processing zone is cycled to amplify the DNA in each bolus. FIG. 6 illustrates the temperature profile of the PCR processing zone, according to some embodiments, as a result of step 408 being performed. As shown in FIG. 6, and as is well known in the art, one temperature cycle consists of: (1) holding the temperature of the PCR processing zone at a first temperature (t1) (e.g., 52 degrees C.) for a first period of time (p1) (e.g., 5 seconds), (2) then rapidly increasing the temperature from t1 to t2 (e.g., 72 degrees C.) and holding the temperature at t2 for a second period of time (p2) (e.g., 10 seconds), (3) then rapidly increasing the temperature from t2 to t3 (e.g., 94 degrees C.) and holding the temperature at t3 for a third period of time (p3) (e.g., 5 seconds), and (4) then rapidly dropping the temperature back to t1 so that the cycle may repeat. The above described temperature cycle may be referred to as a "PCR cycle." In some embodiments, the PCR cycles repeat for period of time (e.g., as long as necessary to produce a sufficient amount of DNA—typically about 20-40 PCR cycles).

In step 410, image sensor 108 is used to capture images of at least one bolus within the PCR processing zone as the bolus moves through the zone and as the temperature of the zone is cycled as described above. In some embodiments, the images are captured only during the "middle" of the PCR cycle (i.e., the time during which the temperature is held at t2), as shown in FIG. 6. In some embodiments, sensor controller 110 controls the image capturing and windows images sensor 108 so that the step of capturing an image of the bolus includes reading only the pixels of the image sensor 108 that are within image sensor region 121, or a subset of those pixels, such as, for example, the pixels that receive light from the bolus and one or more immediately surrounding pixels.

In step 412, the images captured in step 410 are processed by, for example, image processing system 112. Image processing system 412 may include one or more processors programmed by software to determine the intensity of fluorescence emitted from the bolus as a function of time.

Figure 7:
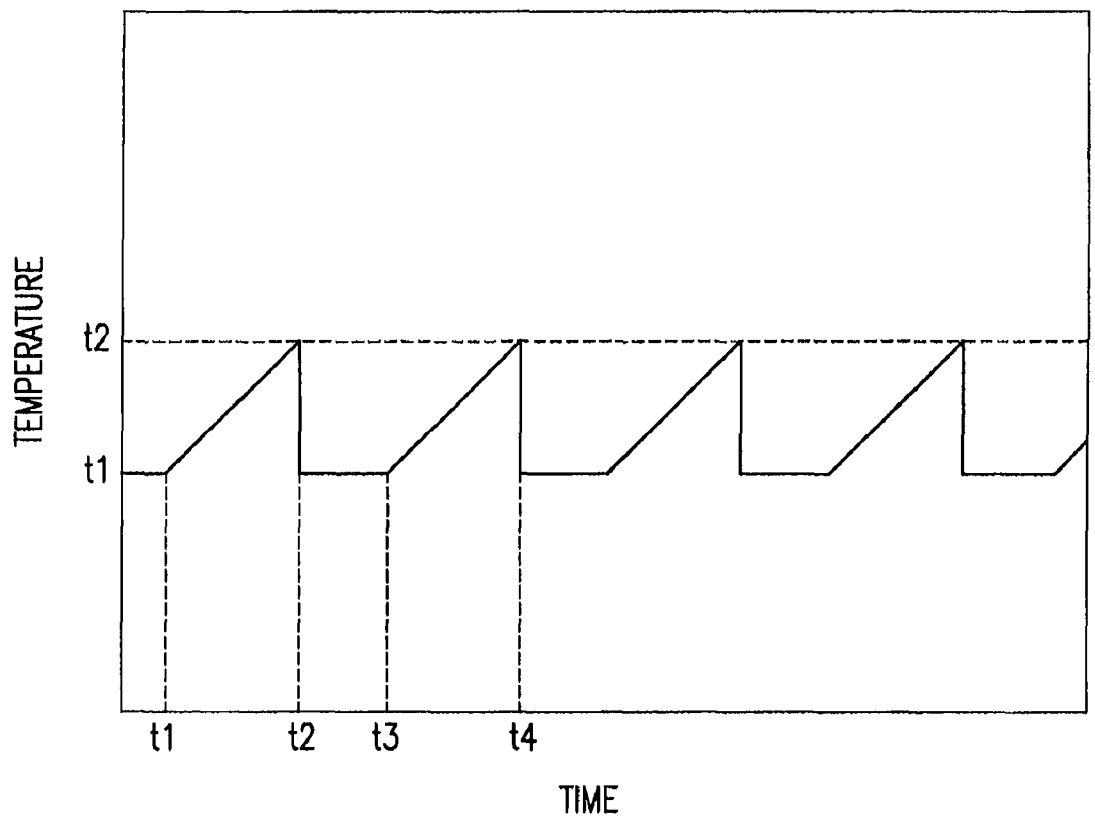
FIG. 7 illustrates a second temperature profile according to one embodiment.

In step 418, when (or shortly after) a bolus enters the HRTm analysis zone and while it moves though the zone, the temperature of the HRTm analysis zone is increased to cause dsDNA within the bolus to transition to ssDNA. FIG. 7 illustrates the temperature profile of the HRTm analysis zone, according to some embodiments. In the example shown in FIG. 7, a first bolus enters the HRTm analysis zone at (or shortly after) time t1 and remains within the zone until (or shortly after) time t2 and a second bolus enters the HRTm analysis zone at (or shortly after) time t3 and remains within the zone until (or shortly after) time t4. As shown in FIG. 7, while the first and second samples are within the HRTm analysis zone, the temperature of the zone may increase, at a substantially constant rate (e.g., 0.1 to 1 degrees C. per second), from temperature t1 (e.g., about 65 degrees C.) to temperature t2 (e.g., about 95 degrees C.), which temperature increase should cause dsDNA within the samples to transition to ssDNA.

In one embodiment, amplification by PCR is performed in the presence of a dsDNA binding fluorescent dye. The dye does not interact with ssDNA but actively binds with dsDNA and fluoresces brightly in this state. This shift in fluorescence can be used firstly to measure the increase in DNA concentration in the PCR processing zone and then to directly measure thermally-induced DNA dissociation by HRTm. Initially, fluorescence is high in a melt analysis because the sample starts as dsDNA, but fluorescence diminishes as the temperature is raised and DNA dissociates into single strands. The observed "melting" behavior is characteristic of a particular DNA sample. A melt curve is typically made and plots the transition from high fluorescence of the initial pre-melt phase through the sharp fluorescence decrease of the melt phase to basal fluorescence at the post-melt phase. Fluorescence decreases as DNA binding dye is released from double-stranded DNA as it dissociates (melts) into single strands. The midpoint of the melt phase, at which the rate of change in fluorescence is greatest, defines the temperature of melting (TM) of the particular DNA fragment under analysis.

Suitable dsDNA binding dyes included SYBR® Green 1 (Invitrogen Corp., Carlsbad, Calif.), SYTO® 9 (Invitrogen Corp., Carlsbad, Calif.), LC Green® (Idaho Technologies, Salt Lake City, Utah) and Eva Green™ (Biotium Inc, Hayward, Calif.). Of these dyes, SYTO® 9, LC Green® and Eva Green™ have low toxicity in an amplification reaction and can therefore be used at higher concentrations for greater saturation of the dsDNA sample. Greater dye saturation means measured fluorescent signals have higher fidelity, apparently because there is less dynamic dye redistribution to non-denatured regions of the nucleic strand during melting and because dyes do not favor higher melting temperature products (Wittwer et al., *Clinical Chemistry* 49:853-860 (2003)). The combination of these characteristics provides greater melt sensitivity and higher resolution melt profiles.

In step 420, image sensor 108 is used to capture images of the bolus within the HRTm analysis zone as the bolus moves through the zone and while the temperature of the zone is increased as described above. In some embodiments, when the image sensor is used to capture images of the bolus within the HRTm analysis zone the image sensor is in the same position and orientation it was in when it was used in step 410 to capture images of the bolus within the PCR processing zone.

In some embodiments, in step 420, the images are captured at a high frame rate (e.g., more than 5 images per second and preferably at least about 10 images per second). In some embodiments, sensor controller 110 controls the image capturing and windows images sensor 108 so that the step of capturing an image of the bolus includes reading only the pixels of the image sensor 108 that are within image sensor region 122, or a subset of those pixels, such as, for example, the pixels that receive light from the bolus and one or more immediately surrounding pixels.

In step 422, the images captured in step 420 are processed by, for example, image processing system 112. Image processing system 412 may include one or more processors programmed by software to determine the intensity of fluorescence emitted from the bolus as a function of time.

As illustrated in FIG. 4, steps 418-420 may occur simultaneously with steps 408-410.

While various embodiments/variations of the present invention have been described above, it should be understood that they have been presented by way of example only, and not limitation. Thus, the breadth and scope of the present invention should not be limited by any of the above-described exemplary embodiments.

Additionally, while the process described above and illustrated in FIG. 4 is shown as a sequence of steps, this was done solely for the sake of illustration. Accordingly, it is contemplated that some steps may be added, some steps may be omitted, and the order of the steps may be re-arranged.

For the claims below the words "a" and "an" should be construed as "one or more."

What is claimed is:

1. A system, comprising:
   a microfluidic channel comprising a PCR processing zone and an HRTm analysis zone; and
   an image sensor having a first image sensor region having a first field of view and a second image sensor region having a second field of view, wherein the second field of view is different than the first field of view, wherein
   at least a portion of the PCR processing zone is within the first field of view, and
   at least a portion of the HRTm analysis zone is within the second field of view.

2. The system of claim 1, further comprising:
   a first thermal generating apparatus configured to provide heat to and/or absorb heat from the PCR processing zone; and
   a second thermal generating apparatus configured to provide heat to and/or absorb heat from the HRTm analysis zone.

3. The system of claim 2, wherein the first thermal generating apparatus is configured to cycle the temperature in the PCR processing zone when a bolus of solution containing real-time PCR reagents is within the PCR processing zone in order to achieve PCR.

4. The system of claim 3, wherein the first thermal generating apparatus is configured such that, after the bolus enters the PCR processing zone for PCR processing, the first thermal generating apparatus heats the bolus to a first temperature, cools the bolus to a second temperature, and heats the bolus to a third temperature.

5. The system of claim 4, wherein, the second thermal generating apparatus is configured to provide to the bolus a substantially steadily increasing amount of heat at a thermal ramp rate of between about 0.1 to 1 degree Celsius (C.) per second.

6. The system of claim 1, further comprising a lens disposed between the channel and the image sensor, wherein the lens is configured to focus onto the first image sensor region light coming from the PCR processing zone and focus onto the second image sensor region light coming from the HRTm analysis zone.

7. The system of claim 1, further comprising an excitation source for producing electromagnetic radiation directed at the channel.

8. The system of claim 1, wherein the HRTm analysis zone is operable to receive a plurality of spaced apart boluses of solution containing real-time PCR reagents.

9. The system of claim 8, further comprising an image sensor controller configured such that, for each of said bolus that undergoes HTRm processing in the HRTm analysis zone, the image sensor controller captures at least about 10 images per second from the second image sensor region for at least about 1 minute while the bolus undergoes the HRTm analysis.

10. The system of claim 9, wherein the image sensor controller is further configured so that, for each said bolus that undergoes PCR processing in the PCR processing zone, the controller captures at least about 1 image every 90 seconds from the first image sensor region for at least about 10 minutes while the bolus is undergoing the PCR processing.

11. The system of claim 9, wherein the image sensor controller is further configured so that, for each said bolus that undergoes PCR processing in the PCR processing zone, the controller captures not more than 1 image every 1 second from the first image sensor region for at least about 10 minutes while the bolus undergoes the PCR processing.

12. In a system comprising (a) an image sensor and (b) a microfluidic channel comprising a PCR processing zone and a separate HRTm analysis zone, a method, comprising:
   (a) using the PCR processing zone of the channel to achieve PCR;
   (b) using the HRTm analysis zone of the channel to perform an HRTm process;
   (c) while performing step (b), using the image sensor to obtain images of the HRTm analysis zone; and
   (d) after performing step (c) and without moving the image sensor from the position it was in relative to the channel when step (c) was performed, using the image sensor to obtain images of the PCR processing zone while performing step (a).

13. The method of claim 12, wherein the step of using the PCR processing zone to achieve PCR comprises:
   moving a bolus of test solution containing real-time PCR reagents through the PCR processing zone; and
   while the bolus is in the PCR processing zone, cycling the temperature of the bolus.

14. The method of claim 13, wherein the step of cycling the temperature of the bolus comprises heating the bolus to a first temperature, cooling the bolus to a second temperature, and heating the bolus to a third temperature.

15. The method of claim 13, wherein the step of using the HRTm analysis zone to perform an HRTm process comprises:
   moving a bolus of test solution containing real-time PCR reagents through the HRTm analysis zone; and
   while the bolus is in the HRTm analysis zone, steadily increasing the temperature of the bolus.

16. The method of claim 15, wherein:
   the step of cycling the temperature of the bolus in order to achieve PCR comprises using a first thermal generating apparatus to cycle the temperature, and
   the step of steadily increasing the temperature of the bolus comprises using a second thermal generating apparatus to steadily increase the temperature.

17. The method of claim 12, further comprising using a lens to focus onto a first portion of the image sensor light coming from the PCR processing zone and to focus onto a second portion of the image sensor light coming from the HRTm analysis zone.

18. The method of claim 12, further comprising using an excitation source to supply electromagnetic radiation to the PCR processing zone of the channel.

19. The method of claim 12, further comprising causing a bolus of solution containing real-time PCR reagents to move through the PCR processing zone and then through the HRTm analysis zone.

20. The method of claim 19, further comprising:
using the image sensor to capture at least about 10 images of the bolus per second for at least about 1 minute while the bolus is in the HRTm analysis zone.

21. The method of claim 20, further comprising:
using the image sensor to capture at least about 1 image of the bolus every 90 seconds for at least about 10 minutes while the bolus is in the PCR processing zone.

* * * * *